US00PP21225P3

(12) United States Plant Patent
Seguel Benitez et al.

(10) Patent No.: US PP21,225 P3
(45) Date of Patent: Aug. 24, 2010

(54) MURTILLA PLANT NAMED 'SOUTH PEARL—INIA'

(50) Latin Name: ***Ugni molinae* Turcz. (syn. *Myrtus ugni*)**
Varietal Denomination: South Pearl—INIA

(75) Inventors: Ivette Seguel Benitez, Temuco (CL); Adolfo Montenegro Barriga, Temuco (CL)

(73) Assignee: Instituto De Investigaciones Agropecuarias, Santiago (CL)

( * ) Notice: Subject to any disclaimer, the term of this patent is extended or adjusted under 35 U.S.C. 154(b) by 0 days.

(21) Appl. No.: 12/077,727

(22) Filed: Mar. 19, 2008

(65) Prior Publication Data

US 2008/0313781 P1 Dec. 18, 2008

(30) Foreign Application Priority Data

Mar. 19, 2007 (CL) ..... 732

(51) Int. Cl.
*A01H 5/00* (2006.01)

(52) U.S. Cl. ..... Plt./226

(58) Field of Classification Search ..... Plt./226, Plt./156

See application file for complete search history.

(56) References Cited

OTHER PUBLICATIONS

The New Royal Horticultural Society Dictionary of Gardening; 1992; vol. 4, (R to Z); p. 543.*

* cited by examiner

*Primary Examiner*—Susan B McCormick Ewoldt
(74) *Attorney, Agent, or Firm*—Ballew Law

(57) ABSTRACT

'South Pearl—INIA' is a new variety of murtilla plant, characterized by intense red berries having excellent flavor, appearance, and shipping and storage qualities.

2 Drawing Sheets

CROSS-REFERENCE TO RELATED APPLICATIONS

None

PRIORITY CLAIM

This application claims priority under 35 U.S.C. §119(f) of Chilean Plant Variety Rights Application Ser. No. 732, filed Mar. 19, 2007.

STATEMENT REGARDING FEDERALLY SPONSORED RESEARCH OR DEVELOPMENT

None

Genus and species: *Ugni molinae* Turcz. (syn. *Myrtus ugni*).

Variety denomination: South Pearl—INIA.

BACKGROUND OF THE INVENTION

The murtilla plant, also known as "Chilean guava" or "uñi," is native to Southern Chile. Fruit of the murtilla plant is used for fresh consumption, as well as for processing into jellies, syrups, desserts, and liqueurs. Until recently, commercially harvested murtilla fruit was obtained from wild murtilla plants, as there were no known, cultivated murtilla plants having the specific characteristics desireable for commercial production.

In 1996, a research project was initiated to domesticate murtilla and develop selections suitable for commercial production. The research project involved the creation of a murtilla gene bank, the first such collection in Chile, as well as the study of suitable reproduction techniques; phenotypic characterization of the germplasm collection; evaluation of the chemical characteristics of the fruit; molecular characterization of the fruit; reproductive studies; agronomic evaluations; development of agronomic management guides; identification and development of new varieties; and economic and commercial studies. As a result of the murtilla research project, several new varieties of murtilla plant were identified and selected for advancement and commercialization.

'South Pearl—INIA' is a new variety of murtilla plant developed-through a murtilla research project. In 1996, germplasm samples were obtained from 103 murtilla plants at 36 collection sites in southern Chile. These samples were then cultivated at a testing facility in Chile for observation and testing as described above. After extensive evaluation and successive asexual propagations through rooted cuttings at the testing and evaluation facilities at, Carillanca, Temuco, Chile, 'South Pearl—INIA' was identified by the inventors as having characteristics that distinguish it from other murtilla plants, and make it particularly suitable for commercial production. The observed plant retains its distinctive characteristics and reproduces true to type in successive generations.

'South Pearl—INIA' is distinguishable from wild murtilla and from its sister plant ('Red Pearl—INIA', application-12/077,728). Table 1 sets forth some of the distinguishing characteristics of 'South Pearl—INIA.'

TABLE 1

Comparison of 'Red Pearl-INIA' to 'South Pearl-INIA' and to wild murtilla

| | Red Pearl-INIA | South Pearl-INIA | Wild murtilla (avg.) |
|---|---|---|---|
| Skin Color | Intense dark red | Light Red | Red |
| Fruit Size | 1.0 | 1.0 | 1.0 to 1.5 cm |
| Harvest Yield | 11.1 kg/plant | 0.9 kg/plant | 0.6 kg/plant |

TABLE 2

Comparison of 'Red Pearl-INIA' to 'South Pearl-INIA' and to wild murtilla. Fruit yielding per plant (g) of ten genotypes of murtilla evaluated at Port Saavedra, Curaco, El Tirol and Huincacara localities, IX Region, and Corte Alto y Ensenada localities, X Region. Second Season.

| Genotypes/varieties | Puerto Saavedra | Curaco | El Tirol | Huincacara | Corte Alto | Ensenada |
|---|---|---|---|---|---|---|
| 14-4 | 73.7 g | 164.0 g | 71 g | 30 g | 21.1 g | 11.8 g |
| 16-2 | 40.2 g | 50.5 g | 58 g | 19 g | 3.8 g | 19.0 g |
| 17-2 | 33.7 g | 131.7 g | 99 g | 25 g | 13.1 g | 11.9 g |
| 18-1 | 100.4 g | 98.7 g | 70 g | 29 g | 11.4 g | 8.9 g |
| Red Pearl INIA | 409.8 g | 115.5 g | 112 g | 47 g | 38.2 g | 33.4 g |
| 22-1 | 217.9 g | 110.2 g | 102 g | 19 g | 10.0 g | 14.5 g |
| 23-2 | 352.2 g | 52.9 g | 127 g | 30 g | 47.7 g | 22.5 g |
| South Pearl INIA | 463.9 g | 111.6 g | 140 g | 42 g | 23.8 g | 21.3 g |
| 28-1 | N/A | 61.2 g | 78 g | 27 g | 3.5 g | N/A |
| 33-5 | 127 g | 101.2 g | N/A | N/A | 14.9 g | 14.9 g |

BRIEF SUMMARY OF THE INVENTION

'South Pearl—INIA' is a new variety of murtilla plant, characterized by intense dark red berries having excellent flavor, appearance, and shipping and storage qualities.

BRIEF DESCRIPTION OF THE PHOTOGRAPHS

Figure 1:
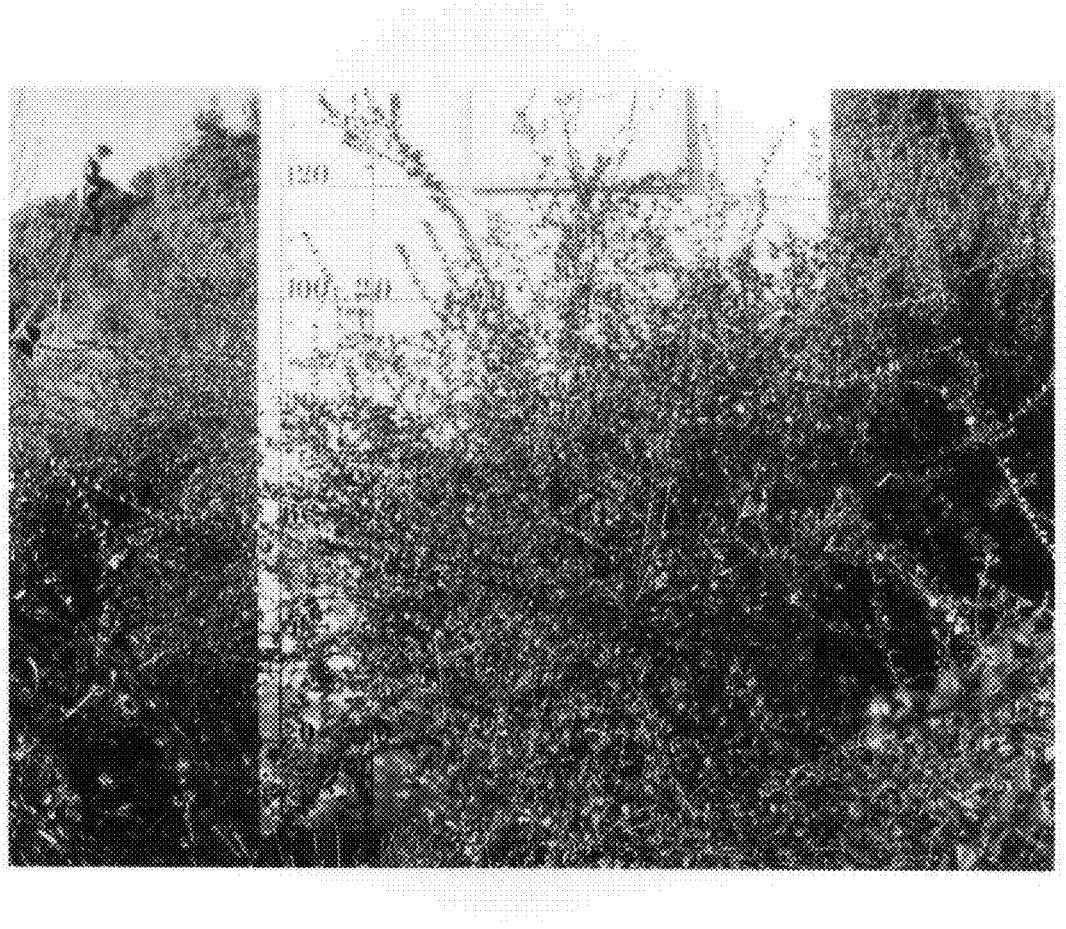
FIG. 1 shows a four year old 'South Pearl—INIA' murtilla plant.
Figure 2:
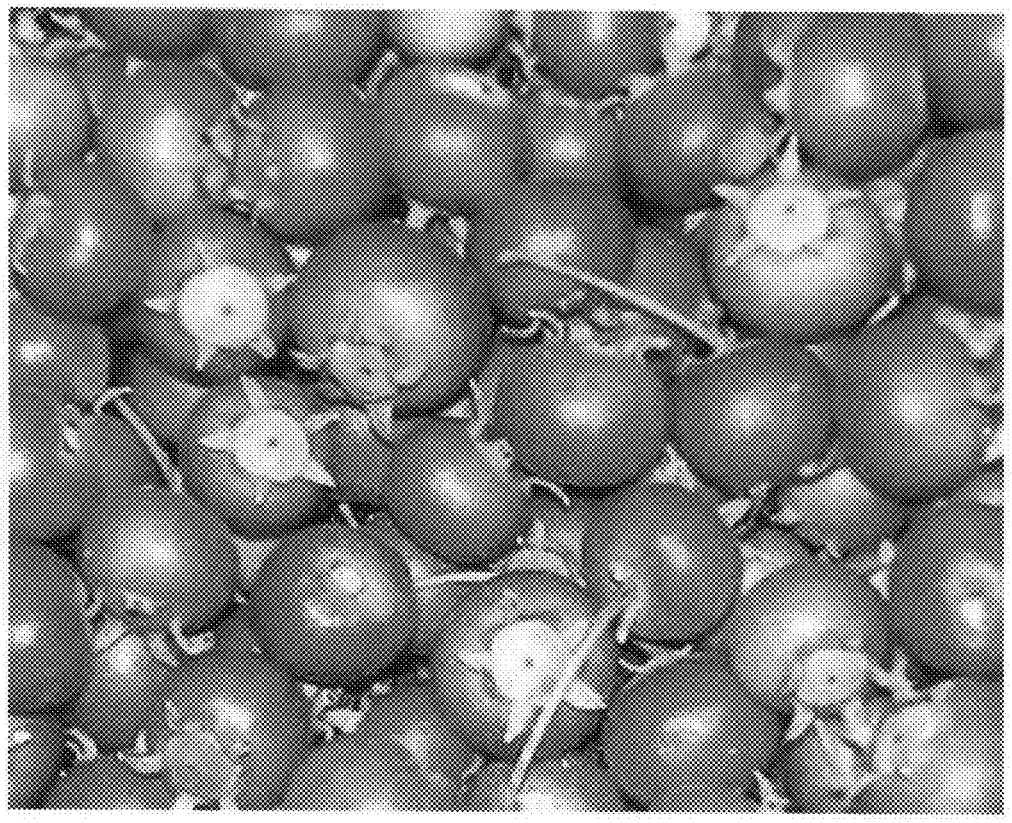
FIG. 2 shows the fruit of a four year old 'South Pearl—INIA' murtilla plant.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed botanical description is primarily based on observations of three year old plants made during the 2005 growing season at a Research Center in Temuco, Chile. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Where color descriptions are provided, reference is made to The Royal Horticultural Society Colour Chart except where general colors of ordinary significance are used.

Parentage:

Parents: Unknown.

Plant:

*Type.*—Evergreen shrub.

*Growth habit.*—Erect.

*Height.*—131 cm.

*Diameter.*—62 cm.

*Internode length.*—13 cm.

Root Development: Three months.

Trunk: Diameter 6.46 mm at 1-2 cm above the ground.

Branch Color: Greyed-Orange 165A.

TABLE 3

Average Height Comparison of 'Red Pearl-INIA' to 'South Pearl-INIA' and to wild murtilla for two seasons in the location of Puerto Saavedra, Chile

| Genotypes | Second Season 2005 | Third Season 2006 |
|---|---|---|
| 14-4 | 86.1 cm | 102.1 cm |
| 16-2 | 56.7 cm | 60.7 cm |
| 17-2 | 103.7 cm | 115.5 cm |
| 18-1 | 90.2 cm | 111.2 cm |
| 'Red Pearl-INIA' | 114.7 cm | 130.6 cm |
| 22-1 | 111.9 cm | 135.1 cm |
| 23-2 | 111.7 cm | 131.8 cm |
| 'South Pearl-INIA' | 117.2 cm | 129.2 cm |
| 28-1 | 66.7 cm | 79.8 cm |
| 33-5 | 99.8 cm | 109.7 cm |

Vigor: Average growth of 15.9 cm in one year in the location of Puerto Saavedra, Chile.

Bark Color: Greyed-Orange 165A.

Leaves:

*Length.*—16 mm.

*Width.*—11.88 mm.

*Length to width ratio.*—1:3.

*Shape.*—Deltoid.

*Apex shape.*—Aristulate.

*Base shape.*—Rounded, nearly sessile.

*Arrangement.*—Decussate.

*Texture.*—Smoothly glabrous.

*Color.*—Upper Surface—Green 137A; Lower Surface—Yellow-Green 146C.

*Vein color.*—Yellow-Green 146C.

*Venation pattern.*—Pinnate.

*Petiole length.*—Average Length 3-5 mm.

*Petiole diameter.*—1 mm.

*Petiole color.*—Yellow-Green 152D.

Flowers:

*Type.*—Pentamerous; Solitary; Axillary; Long peduncle.

*Petals.*—Quantity per flower five; Apex shape rounded; Base shape rounded; Average Length—5-6 mm; Average Width of Base —1-2 mm; Average Width of Apex—1-2 mm; Color top surface —Red-Purple 69D; Color bottom surface—Red-Purple 69D.

*Sepals.*—Quantity per flower five.

*Bloom period.*—Bloom dates (calculated from planting date).

*Start of blooming.*—104 days.

*Full bloom.*—154 days.

*End of blooming.*—168 days.

*Color open flower.*—Red-Purple 69D.

*Diameter.*—Diameter of flower bud—5 mm-6 mm; Diameter of fully open flower—0.9-1.1 cm.
*Flowers per cluster.*—2.
*Fragrance.*—Softly sweet floral fragrance.
*Reproductive Organs.*—Hermaphroditic with inferior ovary.
*Anther length.*—Length 1 mm.
*Anther color.*—Apical and lateral edges Yellow-Orange 14C.
*Vein color.*—Red-Purple 62A continuing from the filament part way through the anther.
*Filament length.*—Average length ranges from 0.5 mm to 2 mm.
*Filament color.*—Red-Purple 62A.
*Style length.*—Average length: 4-5 mm.
*Style base color.*—Red-Purple 62C.
*Style apex color.*—Greyed-Yellow 160C.
*Stigma shape.*—Ensiformis.
*Stigma length.*—Average length 1 mm.
*Stigma color.*—Green-142D.
*Pollination requirement.*—Unknown.

Fruit:

*Quantity of seeds per fruit.*—25.5.
*Fruit shape.*—Spherical.
*Diameter* (*avg.*).—1.0 cm (varies between about 0.9 cm and 1.1 cm, depending upon water and fertilizer application).
*Fruit skin color.*—RED 44B.
*Fruit pulp color.*—White 155B.
*Seeds.*—Greyed-Orange 166D.
*Peduncle length.*—12 mm.
*Yield.*—1,142 g/plant.

| Fruit Analytical Data: | |
|---|---|
| Humidity (%) | 76.23 |
| Protein N × 6.25 (%) | 1.08 |
| Ashes (%) | 0.83 |
| Etereus Extract (%) | 0.92 |
| Fiber (%) | 3.24 |
| E.N.N. (%) | 17.69 |
| Pectin (%) | 0.32 |
| Total Sugar (sucrose) (%) | 9.78 |
| Reductors Sugar (glucosa) (%) | 4.65 |
| pH | 3.19 |
| Avg. Soluble Solids (° Brix) (varies by growing region) | 16 |
| Avg. Titratable Acidity (%) (varies by growing region) | 2.2 |

Pest and disease resistance/susceptibility: None noted to date.
Hardiness: Resistant to cold temperatures.
Storageability: 'South Pearl—INIA' has excellent storage capacity up to 28 days post-harvest.

It is claimed:

1. What is claimed is a new and distinct murtilla plant as shown and described herein.

* * * * *